US010702127B2

(12) United States Patent
Makino

(10) Patent No.: US 10,702,127 B2
(45) Date of Patent: Jul. 7, 2020

(54) ENDOSCOPE SYSTEM AND EVALUATION VALUE CALCULATION DEVICE

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 216 days.

(21) Appl. No.: 15/553,966

(22) PCT Filed: Jun. 24, 2016

(86) PCT No.: PCT/JP2016/068908
§ 371 (c)(1),
(2) Date: Mar. 23, 2018

(87) PCT Pub. No.: WO2016/208748
PCT Pub. Date: Dec. 29, 2016

(65) Prior Publication Data
US 2018/0184882 A1 Jul. 5, 2018

(30) Foreign Application Priority Data
Jun. 25, 2015 (JP) ................ 2015-128001

(51) Int. Cl.
*A61B 1/00* (2006.01)
*A61B 1/04* (2006.01)
(Continued)

(52) U.S. Cl.
CPC ...... *A61B 1/00009* (2013.01); *A61B 1/00048* (2013.01); *A61B 1/04* (2013.01);
(Continued)

(58) Field of Classification Search
CPC ... A61B 1/00009; A61B 1/00048; A61B 1/04; G06T 7/0012; G06T 2207/10024; G06T 2207/10068; G06T 2207/30004
See application file for complete search history.

(56) References Cited

U.S. PATENT DOCUMENTS 4,961,110 A 10/1990 Nakamura
6,128,144 A * 10/2000 Togino .............. G02B 7/10
359/728
(Continued)

FOREIGN PATENT DOCUMENTS

JP H02-224635 A 9/1990
JP H04-090285 A 3/1992
(Continued)

OTHER PUBLICATIONS

International Preliminary Report on Patentability dated Dec. 26, 2017, for International Application No. PCT/JP2016/068908.
(Continued)

*Primary Examiner* — Mishawn N. Hunter
(74) *Attorney, Agent, or Firm* — Kilpatrick Townsend & Stockton LLP

(57) ABSTRACT

This endoscope system comprises: an image acquiring means for acquiring a color image having at least three color components; a placement means for placing points corresponding to respective pixels forming the color image in accordance with the color components of the points, within a plane including a first axis that is an axis of a first component among the at least three color components and a second axis that is an axis of a second component among the at least three color components and that intersects with the first axis; a distance data calculating means for calculating data regarding the distances between the points corresponding to respective pixels and a third axis defined as an axis that passes through a point at which the first axis and the second axis intersect with each other in the plane and that is not parallel to the first axis and the second axis; and an evaluation value calculating means for calculating a certain evaluation value for the color image on the basis of the calculated distance data.

16 Claims, 5 Drawing Sheets

(51) Int. Cl.
*A61B 1/05* (2006.01)
*A61B 1/06* (2006.01)
*A61B 1/07* (2006.01)
*G06T 7/00* (2017.01)

(52) U.S. Cl.
CPC .............. *A61B 1/05* (2013.01); *A61B 1/0669* (2013.01); *A61B 1/07* (2013.01); *G06T 7/0012* (2013.01); *G06T 2207/10024* (2013.01); *G06T 2207/10068* (2013.01); *G06T 2207/30004* (2013.01)

(56) References Cited

U.S. PATENT DOCUMENTS

| | | | |
|---|---|---|---|
| 2003/0071895 A1 | 4/2003 | Ayame et al. | |
| 2005/0013370 A1* | 1/2005 | Kim | H04N 11/042 375/240.16 |
| 2005/0281473 A1* | 12/2005 | Kim | H04N 19/105 382/236 |
| 2009/0109284 A1 | 4/2009 | Takayama et al. | |
| 2011/0273548 A1* | 11/2011 | Uchiyama | A61B 1/00009 348/68 |
| 2012/0033105 A1* | 2/2012 | Yoshino | A61B 1/00009 348/239 |
| 2012/0265041 A1* | 10/2012 | Yamaguchi | A61B 1/00004 600/328 |
| 2013/0051642 A1 | 2/2013 | Kono et al. | |
| 2014/0320620 A1 | 10/2014 | Yoshino et al. | |
| 2015/0193929 A1 | 7/2015 | Ikemoto | |
| 2016/0007829 A1 | 1/2016 | Chun | |
| 2016/0174886 A1 | 6/2016 | Shiraishi | |

FOREIGN PATENT DOCUMENTS

| | | |
|---|---|---|
| JP | H09-035056 A | 2/1997 |
| JP | 2003-093337 A | 4/2003 |
| JP | 5006759 B | 5/2009 |
| JP | 5006759 B2 | 8/2012 |
| JP | 2013-051988 A | 3/2013 |
| JP | 2014-018332 A | 2/2014 |
| JP | 2014-213094 A | 11/2014 |
| JP | 5647752 B | 1/2015 |
| JP | 2015-85152 A | 5/2015 |

OTHER PUBLICATIONS

International Search Report dated Sep. 27, 2016, for International Application No. PCT/JP2016/068908.

* cited by examiner

ENDOSCOPE SYSTEM AND EVALUATION VALUE CALCULATION DEVICE

CROSS-REFERENCE TO RELATED APPLICATIONS

This application claims the benefit of priority under 35 U.S.C. § 371 of International Application No. PCT/JP2016/068908 filed on Jun. 24, 2016 which claims priority to Japanese Application No. 2015-128001 filed Jun. 25, 2015, which is incorporated herein fully by reference in its entirety.

TECHNICAL FIELD

The present disclosure relates to an endoscope system and an evaluation value calculation device which calculate a predetermined evaluation value.

BACKGROUND ART

In general, a lesion portion shows a color different from the color of a normal mucosal tissue. In accordance with improvement of performance of a color endoscope device in recent years, it has become possible for an operator to conduct diagnosis by visually recognizing a lesion portion having a color only slightly different from the color of a normal tissue. However, in order for the operator to conduct diagnosis by visually recognizing a lesion portion precisely from a normal tissue in accordance with a slight color difference on a captured image obtained by an endoscope, the operator needs to be trained for a long period under guidance of an expert. Even for an expert, it is not easy to conduct diagnosis by visually recognizing a lesion portion based on a slight color difference, and therefore cautious work is required in the diagnosis.

In view of the above, for example, Japanese Patent Provisional Publication No. 2014-18332A (hereafter, referred to as patent document 1) describes an apparatus configured to execute scoring for a lesion portion on a captured image so as to assist diagnosis of the lesion portion by an operator. Specifically, the apparatus described in the patent document 1 executes a tone enhancement process in which a nonlinear gain is applied to pixel values of pixels constituting a captured image obtained by an endoscope so as to enhance a dynamic range in a portion around a boundary of a region including pixel values judged to be the lesion portion. The apparatus subsequently converts tone-enhanced pixel data in an RGB space defined by R, G and B primary colors into a predetermined color space, such as an HIS color space or an HSV color space, to obtain information on hue and saturation, judges whether each pixel is a pixel of the lesion portion based on the information on hue and saturation, and calculates an evaluation value (a lesion index) based on the number of pixels judged to be the lesion portion.

SUMMARY OF DISCLOSURE

However, there is a drawback that, since a non-linear calculation process, such as a tone enhancement process and a conversion process of a color space, has a heavy processing load, execution of such a process needs a large amount of hardware resources. Furthermore, as a result of execution of the tone enhancement process, the evaluation value of the captured image fluctuates depending on capturing conditions (e.g., how illumination light impinges on a subject) which affect the brightness of the image.

The present disclosure is made in view of the above described circumstance, and an aspect of the present disclosure is to provide an endoscope system and an evaluation value calculation device capable of suppressing a processing load for calculating an evaluation value while suppressing fluctuation of the evaluation value depending on brightness of an image.

An endoscope according to an embodiment of the present disclosure includes an image obtainer that obtains a color image including at least three color components, an allocator that allocates a point corresponding to each of pixels constituting the color image to a plane including a first axis which is an axis of a first component of the at least three color components and a second axis which is an axis of a second component of the at least three color components and intersects with the first axis, the point being allocated to the plane based on the color component of the point, a distance data calculator that defines, in the plane, a third axis which passes through an intersection of the first axis and the second axis and is nonparallel with each of the first axis and the second axis, and calculates distance data representing a distance between the third axis and the point corresponding to each of the pixels, and an evaluation value calculator that calculates a predetermined evaluation value for the color image based on the calculated distance data.

With this configuration above, fluctuation of the evaluation value depending on the brightness of an image can be suppressed, and further, a processing load for calculating the evaluation value can be suppressed.

In the above-described endoscope system, the at least three components may include an R component, a G component and a B component. In this case, the first axis may represent the R component, and the second axis may represent one of the G component and the B component. Further, the allocator may allocate a point corresponding to each of pixels constituting the color image to the plane including the first axis which is an axis of the R component and the second axis which is an axis of one of the G component and the B component based on the color components of the point.

In the above-described endoscope system, the third axis may be an axis forming 45 degrees with respect to the first axis and forming 45 degrees with respect to the second axis in the plane.

In the above-described endoscope system, the distance data calculator may obtain the distance data by subtracting a value of the second axis from a value of the first axis for each of the pixels.

In the above-described endoscope system, the evaluation value calculator may standardize the distance data between the third axis and the point corresponding to each of the pixels calculated by the distance data calculator by using predetermined reference distance data, and may calculate the predetermined evaluation value of an entire color image based on the standardized distance data of each of the pixels.

In the above-described endoscope system, the predetermined evaluation value may include an inflammation evaluation values regarding strength of an inflammation.

The above-described endoscope system may further include an image display that displays an image in which pixels of a normal portion and pixels of an inflammation portion are indicated in different colors so as to be distinguished from each other.

An endoscope system according to an embodiment of the present disclosure includes an image obtainer that obtains a color image including at least three color components, and an evaluation value calculator that calculates a predetermined evaluation value regarding the color image. In this configuration, the at least three color components includes a first component and a second component, and the evaluation value calculator obtains a subtracted value, for each of pixels constituting the color image, by subtracting the second component from the first component, and calculates the evaluation value based on the subtracted value for each of the pixels constituting the color image.

With the above configuration, fluctuation of the evaluation value depending on the brightness of an image can be suppressed, and further, a processing load for calculating the evaluation value can be suppressed.

In the above-described endoscope system, the first component may be an R component and the second component may be one of a G component and a B component.

An evaluation value calculating device according to an embodiment of the present disclosure includes an allocator that allocates a point corresponding to each of pixels constituting a color image including at least three color components to a plane including a first axis which is an axis of a first component of the at least three color components and a second axis which is an axis of a second component of the at least three color components and intersects with the first axis, the point being allocated to the plane based on the color component of the point, a distance data calculator that defines, in the plane, a third axis which passes through an intersection of the first axis and the second axis and is nonparallel with each of the first axis and the second axis, and calculates distance data representing a distance between the third axis and the point corresponding to each of the pixels, and an evaluation value calculator that calculates a predetermined evaluation value for the color image based on the calculated distance data.

With the above configuration, fluctuation of the evaluation value depending on the brightness of an image can be suppressed, and further, a processing load for calculating the evaluation value can be suppressed.

An evaluation value calculation device according to an embodiment of the present disclosure includes an allocator that allocates a point corresponding to each of pixels constituting a color image having Red, Green and Blue components to a plane including a first axis being an axis of the R component and a second axis which is an axis of the R component or the B component and is perpendicular to the first axis, the point being allocated to the plane based on the Red, Green and Blue components of the point, a distance data calculator that defines, in the plane, a third axis which passes through an intersection of the first axis and the second axis and is nonparallel with each of the first axis and the second axis, and calculates distance data representing a distance between the third axis and the point corresponding to each of the pixels, and an evaluation value calculator that calculates a predetermined evaluation value for the color image based on the calculated distance data.

With the above configuration, fluctuation of the evaluation value depending on the brightness of an image can be suppressed, and further, a processing load for calculating the evaluation value can be suppressed.

In the above-described evaluation value calculation device, the third axis may form 45 degrees with respect to the first axis and may form 45 degrees with respect to the second axis in the plane.

In the above-described evaluation value calculation device, the distance data calculator may obtain the distance data by subtracting a value of the second axis from a value of the first axis for each of the pixels.

In the above-described the evaluation value calculation device, the evaluation value calculator may configured to standardize the distance data between the third axis and the point corresponding to each of the pixels calculated by the distance data calculator by using predetermined reference distance data, and calculates the predetermined evaluation value of an entire of the color image based on the standardized distance data of each of the pixels.

An evaluation value calculation device according to an embodiment of the present disclosure includes a subtractor that obtains a value calculated by subtracting a G component from an R component for each of pixels constituting a color image having R, G and B components, and an evaluation value calculator that calculates a predetermined evaluation value for the color image based on the value obtained by the subtractor.

With the above configuration, fluctuation of the evaluation value depending on the brightness of an image can be suppressed, and further, a processing load for calculating the evaluation value can be suppressed.

In the above-described evaluation value calculation device, the subtractor may be configured to subtract the B component from the R component instead of subtracting the G component from the R component.

DESCRIPTION OF EMBODIMENTS

Hereinafter, an embodiment of the present disclosure is described with reference to the accompanying drawings. In the following explanation, by way of example, an electronic endoscope system is explained as an embodiment of the disclosure.

<Configuration of Electronic Endoscope System 1>

Figure 1:
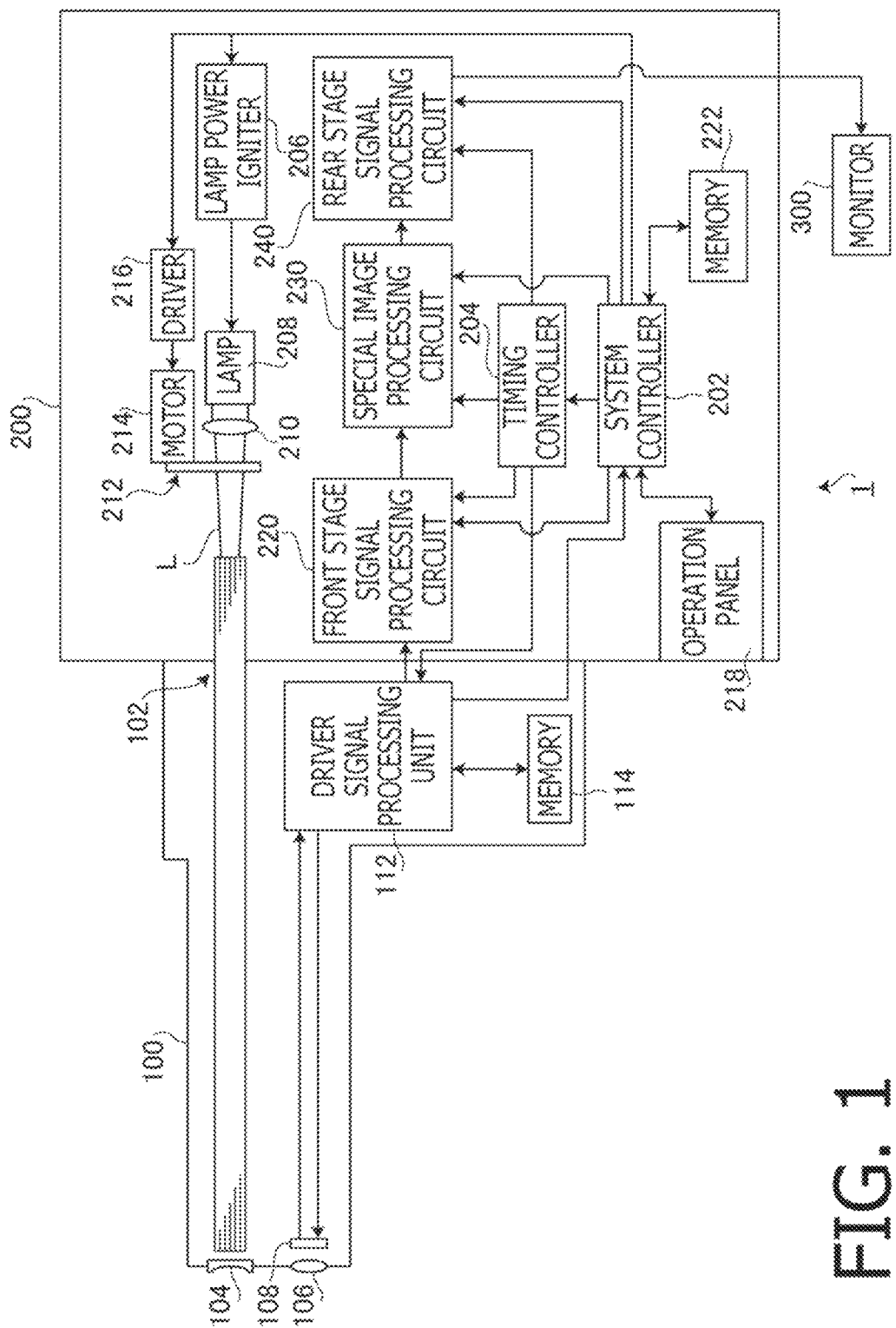
FIG. 1 is a block diagram illustrating a configuration of an electronic endoscope system according to an embodiment of the disclosure.

FIG. 1 is a block diagram illustrating a configuration of an electronic endoscope system 1 according to the embodiment of the disclosure. As shown in FIG. 1, the electronic endoscope system 1 includes an electronic scope 100, a processor 200 and a monitor 300.

The processor 200 includes a system controller 202 and a timing controller 204. The system controller 202 executes various programs stored in a memory 222, and totally controls the electronic endoscope system 1. Further, the system controller 202 is connected to an operation panel 218. In accordance with an instruction input by an operator through the operation panel 218, the system controller 202 changes operations of the electronic endoscope system 1 and parameters for the respective operations of the electronic endoscope system 1. The instructions which could be input by the operator include, for example, an instruction for switching operation modes of the electronic endoscope system 1. In this embodiment, the operation modes include a normal mode and a special mode. The timing controller 204 outputs clock pulses for adjusting timings of the respective operations to each circuit in the electronic endoscope system 1.

A lamp 208 emits white light L after being activated by a lamp power igniter 206. The lamp 208 is a high intensity lamp, such as, a xenon lamp, a halogen lamp, a mercury lamp or a metal-halide lamp, an LED (Light Emitting Diode), laser. The white light L emitted by the lamp 208 is converged by a collecting lens 210 and the light amount of the white light L is limited to an appropriate amount by a diaphragm 212. It is noted that the LED or the laser has characteristics of low power consumption, and small heat generation in comparison with other light sources. Therefore, using the LED or the laser is advantageous since a bright image can be obtained while suppressing the power consumption and/or heat generating amount. To be able to obtain a bright image results in improvement of accuracy of the evaluation vale which will be described later.

To the diaphragm 212, a motor 215 is mechanically connected via a transmission mechanism (not shown), such as an arm and gears. The motor 214 is, for example, a DC motor, and drives the diaphragm 212 under driving control of a driver 216. The diaphragm 212 is activated and a degree of opening of the diaphragm 212 is changed by the motor 214 so that the brightness of a video displayed on a display screen of the monitor 300 is kept appropriate. The amount of the white light L emitted by the lamp 208 is restricted according to the degree of opening of the diaphragm 212. An appropriate brightness reference of video is set and altered in accordance with an adjusting operation of intensity by an operator through the operation panel 218. Since dimmer control circuit configured to adjust the intensity by controlling the driver 216 is well known in the art, explanations thereof will be omitted.

The white light L passed through the diaphragm 212 is converged at an entrance end face of an LCB (Light Carrying Bundle) 102 and enters inside the LCB 102. The white light L which has entered inside the LCB 102 through the entrance end face propagates inside the LCB 102. The white light L which has propagated inside the LCB 102 emerges from an exit end face of the LCB 102 disposed at a tip of the electronic scope 100, and illuminates a living tissue via a light distribution lens 104. Returning light from the living tissue illuminated with the white light L forms an optical image on a light-receiving surface of a solid-state image pickup device 108 through an objective lens 106.

The solid state image pickup device 108 is a single chip color CCD (Charge Coupled Device) image sensor having a Bayer type pixel array. The solid state image pickup device 108 accumulates charges according to a light amount of an optical image converged at each pixel on the light-receiving surface, and generates and outputs image signals of R (Red), G (Green) and B (Blue). Hereinafter, the image signal of each pixel (each pixel address) sequentially output from the solid state image pickup device 108 will be referred to as a "pixel signal". The solid state image pickup device 108 is not limited to a CCD, but may be replaced with a CMOS (Complementary Metal Oxide Semiconductor) image sensor or another type of imaging device. The solid state image pickup device 108 may be of a type which is mounted with complementary color filters. Examples of the complementary color filters include CMYG (cyan, magenta, yellow and green) filters.

Regarding primary color (RGB) filters, since they have good coloring properties in comparison with complementary color filters, and it is possible to improve the evaluation accuracy by using an RGB image signal, which is generated by an image pick up device provided with the primary color filters, for calculating inflammation evaluation value. Further, by using the primary color filters, is becomes unnecessary to convert signals in an inflammation evaluation value calculation, which will be described later. Accordingly, it becomes possible to suppress the processing load in the inflammation evaluation value calculation.

In a connection part of the electronic scope 100, a driver signal processing circuit 112 is provided. To the driver signal processing circuit 112, the pixel signal of the living tissue illuminated with the white light L is input from the solid state image pickup device 118 at the frame cycle. The driver signal processing circuit 112 outputs the pixel signal from the solid state image pickup device 108 to a front stage signal processing circuit 220. In the following explanation, the "frame" may be replaced with a "field". In the present embodiment, the frame cycle and the field cycle are $\frac{1}{30}$ seconds and $\frac{1}{60}$ seconds, respectively.

Further, the driver signal processing circuit 112 accesses a memory 114 to read peculiar information of the electronic scope 100. The peculiar information stored in the memory 114 includes, for example, the pixel number and sensitivity of the solid state image pickup device 108, available frame rates, and a model number. The driver signal processing circuit 112 outputs the peculiar information read from the memory 114 to the system controller 202.

The system controller 202 executes various computations based on the peculiar information of the electronic scope 100 and generates control signals. Using the generated control signals, the system controller 202 controls operation and timings of various circuits in the processor 200 so that processing appropriate to an electronic scope connected to the processor 200 is performed.

The timing controller 204 supplies clock pulses to the driver signal processing circuit 112 in accordance with the timing control by the system controller 202. In accordance with the clock pulses supplied from the timing controller 204, the driver signal processing circuit 112 drives and controls the solid state image pickup device 108 at timings synchronizing with the frame rate of video being processed on the processor 200 side.

<Operation in Normal Mode>

A signal processing operation of the processor 200 in the normal mode will be explained.

The front stage signal processing circuit 220 applies a demosaicing process to each of the R, G and B pixel signals input from the driver signal processing circuit 112 at the frame cycle. Specifically, for each R pixel signal, an interpolation process by G and B peripheral pixels is executed. For each G pixel signal, an interpolation process by R and B peripheral pixels is executed. For each B pixel signal, an interpolation process by R and G peripheral pixels is executed. As a result, the pixel signals each conveying information on one color component are converted into pixel data having information on three color components of R, G and B.

The front stage signal processing circuit 220 applies predetermined signal processing such as a matrix operation, a white balance adjustment process and a gamma correction process to the image data to which the demosaicing process has been applied, and outputs the processed image data to a special image processing circuit 230. An image obtainer for obtaining the color image is configured to include, for example, the solid state image pickup device 108, the driver signal processing circuit 112 and the front stage signal processing circuit 220.

The special image processing circuit 230 through-outputs the image data, which is input from the front stage signal processing circuit 220, to the rear stage signal processing circuit 240.

The rear stage signal processing circuit 240 applies predetermined image processing to the image data input from the special image processing circuit 230 in order to generate screen data for monitor representation, and converts the screen data for monitor representation into a predetermined video format signal. As a result, a color image of the living tissue is displayed on the monitor 300.

<Operation in Special Mode>

Next, a signal processing operation of the processor 200 in the special mode will be explained.

The front stage signal processing circuit 220 applies predetermined signal processes such as the demosaicing process, a matrix calculation, a white balance adjusting process, a gamma compensating process and the like to pixel signals input at every frame period from the driver signal processing circuit 112, and outputs the processed signal to the special image processing circuit 230.

[Special Image Generating Process]

Figure 2:
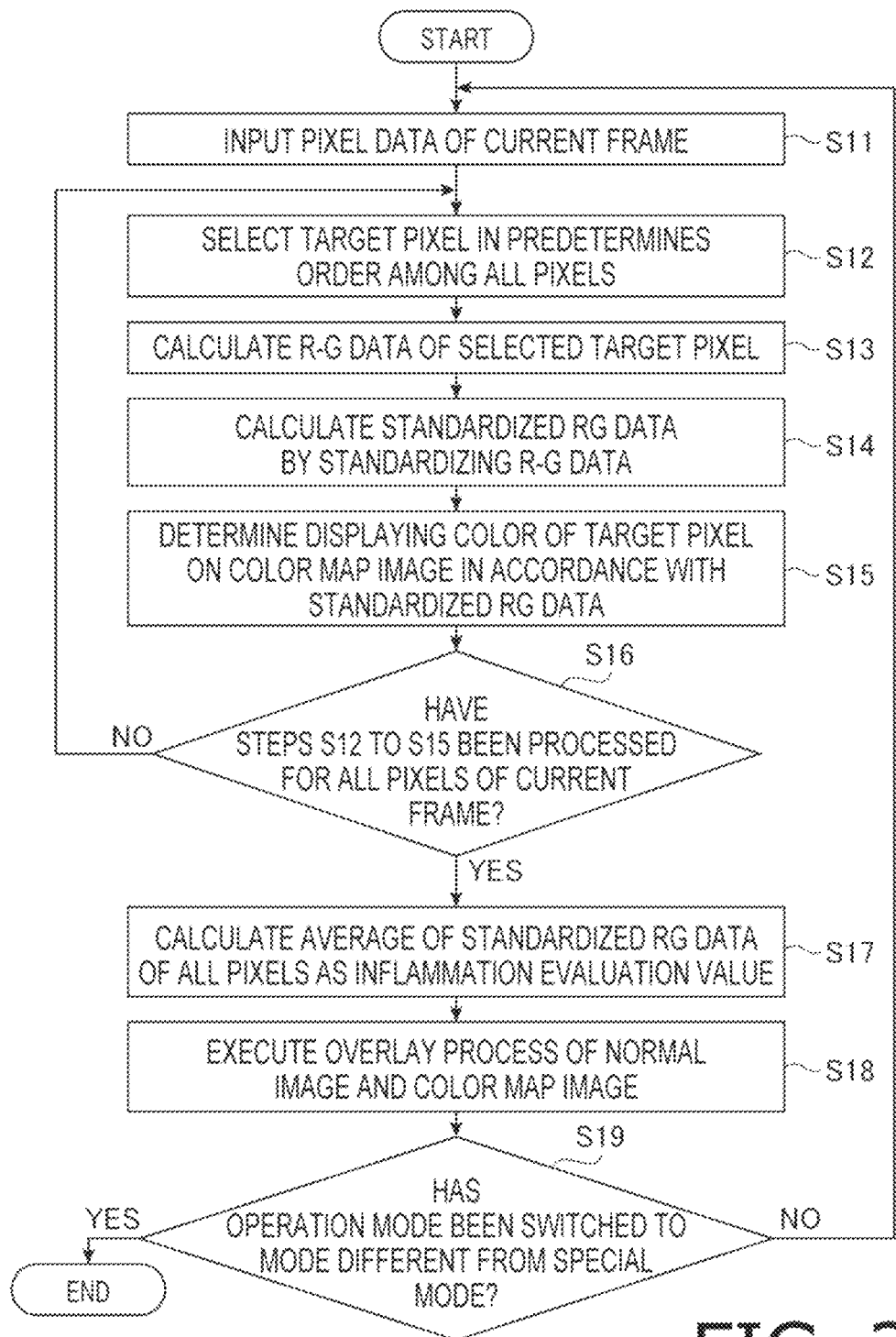
FIG. 2 is a flowchart illustrating a special image generation process executed by a special image processing circuit provided in a processor of the electronic endoscope system according to the embodiment of the disclosure.

FIG. 2 is a flowchart illustrating a special image generation process executed by the special image processing circuit 230. The special image generation process shown in FIG. 2 is started when the operation mode of the electronic endoscope system 1 is switched to the special mode.

<S11 in FIG. 2 (Input of Image Data of Current Frame)>

In block S11, the image data of each pixel of the current frame is input to the special image processing circuit 230 from the front stage signal processing circuit 220.

<S12 in FIG. 2 (Selection of Target Pixel)>

In block S12, one target pixel is selected, from among all the pixels, in accordance with the predetermined order.

<S13 in FIG. 2 (Calculation of R-G Data)>

Figure 3:
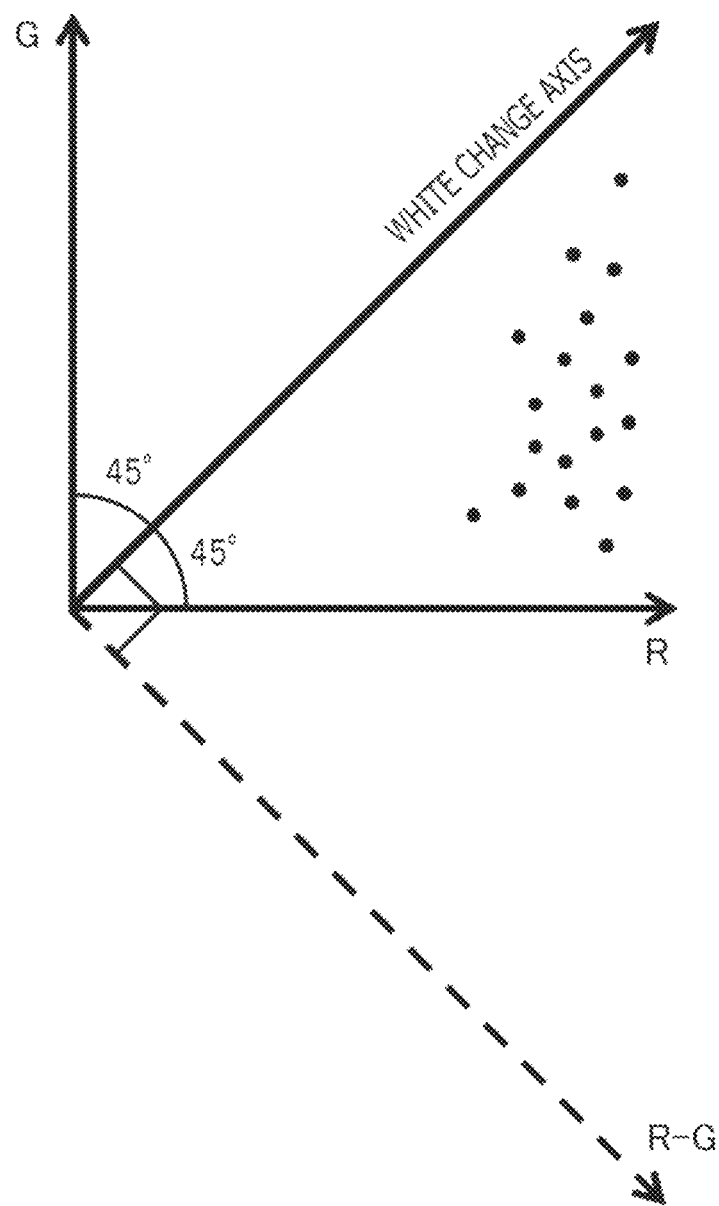
FIG. 3 is an explanatory illustration for supplementary explaining a calculation process for R-G data in block S13 in FIG. 2.
Figure 4:
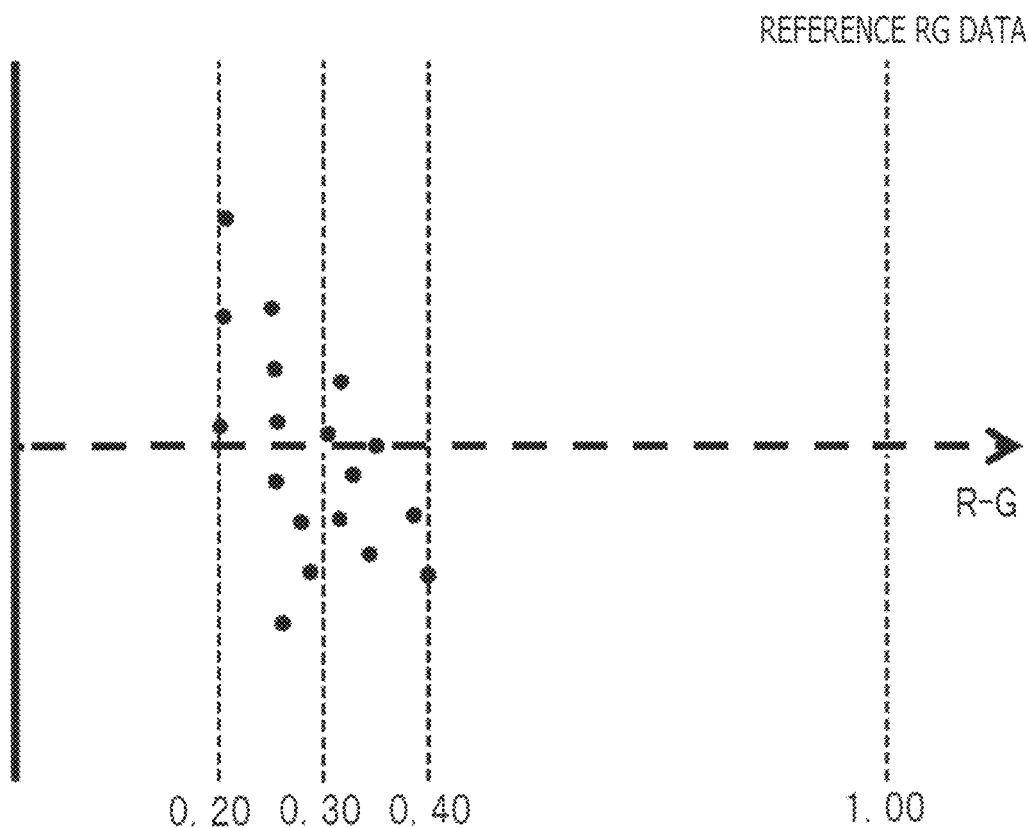
FIG. 4 is an explanatory illustration for supplementary explaining a calculation process for R-G data in block S13 in FIG. 2.

In block S13, R-G data is calculated with respect to the target pixel selected in block S12 (selection of target pixel). FIGS. 3 and 4 are explanatory illustrations for supplementary explaining the calculation process of R-G data.

In FIG. 3, an RG plane defined by an R-axis and a G-axis orthogonally intersecting with each other is illustrated. The R-axis is an axis representing an R component (a pixel value of R), and the G-axis is an axis representing a G component (a pixel value of G). In block S13, target pixel data (three dimensional data) in an RGB space defined by the three primary colors is converted into two dimensional data of R and G, and is plotted on the RG plane according to the pixel values of R and G as shown in FIG. 3. For the sake of explanation, a point of the target pixel data plotted on the RG plane is referred to as a "target pixel corresponding point". It is noted that an operation of allocating the target pixel data in the RG plane executed in S13 is executed by an allocator.

In a body cavity of a patient subject to be an image capturing target, the R component dominates the other components (G and B components) due to effects of hemoglobin coloring matter and etc. Typically, the greater the redness (i.e., the R component) is, the stronger the degree of inflammation is. Therefore, it is basically considered that the value on the R axis of the target pixel is proportional to the strength of inflammation. However, the color tone of a captured image of the inside of the body cavity varies depending on the capturing condition (e.g., how the white light L impinges on the living tissue) which affects the brightness. For example, a shaded portion to which the white light L does not reach becomes black (an achromatic color), while a portion on which the white light strongly impinges and which thereby causes regular reflection becomes white (an achromatic color). That is, depending on how the white light L impinges on the living tissue, the value of the target pixel on the R axis may represent a value that does not correlate to the strength of inflammation.

It is conceivable that, when the brightness of the captured image of the body cavity changes depending on how the white light L impinges on the living tissue, the color tone of the captured image changes basically in the similar manner in each of the R, G and B color components although the color tone of the captured image is affected by individual differences, captured portions and inflammation conditions. For this reason, in this embodiment, an axis (hereafter, referred to as a "white change axis" for convenience of explanation) which passes through an intersection point (an origin) of the R axis and G axis and forms 45 degrees with respect to each of R axis and G axis is defined.

When the brightness of the captured image changes depending on how the white light impinges on the living tissue, the target pixel data (target pixel corresponding point) changes approximately along the white change axis. Therefore, the white change axis can be defined as an axis which is most sensitive to the brightness of the captured image. Regarding an R-G axis (see FIG. 3) orthogonally intersecting with the white change axis, which is the most sensitive to the brightness of the captured image, can be defined as an axis which is most insusceptible to the brightness of the captured image (i.e., an axis not substantially affected by the brightness of the captured image).

According to the above described definitions, a distance between the target pixel corresponding point and the white change axis (a distance along the R-G axis) represents the strength of inflammation and is not substantially affected by the brightness of the captured image (i.e., change of color tone due to the brightness of the captured image is not substantially caused). Therefore, in block S13, for the target pixel selected in block S12 (selection of target pixel), distance data between the white change axis and the target pixel corresponding point is calculated.

More specifically, in block S13, for the target pixel selected in block S12 (selection of target pixel), R-G data, i.e., the distance data (distance along the R-G axis) between the target pixel corresponding point and the white change axis is obtained by executing a simple calculation of subtracting a G pixel value from an R pixel value. It is noted that the process of calculating the distance data between the target pixel corresponding point and the white change axis in S13 is executed by the distance data calculator.

<S14 in FIG. 2 (Standardization Process)>

FIG. 4 illustrates an example of the R-G data (data representing the strength of inflammation) calculated in block S13 (calculation of R-G data). In FIG. 4, the horizontal axis is the axis of the R-G data. In this embodiment, a reference to the R-G data is defined based on the idea that the strongest inflammation corresponds to a state where the inflammation has advanced and therefore blood itself is being observed. In the following, for convenience of explanation, the reference to the R-G data is referred to as a "reference RG data". The reference RG data is an average value of R-G data of a plurality of samples of blood images captured in advance.

In block S14, the R-G data calculated in block S13 (calculation of R-G data) is standardized to be a value defined when the reference RG data is 1.00. In the following, for convenience of explanation, the standardized RG data is referred to as a "standardized RG data". In the example shown in FIG. 4, the standardized RG data is distributed within a range of 0.20 to 0.40.

<S15 in FIG. 2 (Determination of Displaying Color on Color Map Image)>

In this embodiment, a color map image obtained by performing mosaicing for the captured image with displaying colors corresponding to the respective strengths of inflammation can be displayed. To enable displaying of the color map image, a table in which the displaying colors are related to the values of the standardized RG data is stored for example in the memory 222. For example, in the table, the values of the standardized RG data are related to the displaying colors at intervals of 0.05. Illustratively, the range of 0.00 to 0.05 of the value of the standardized RG data is associated with yellow, and each time the value of the standardized RG data increases by 0.05, a different displaying color in the order of the color circle is associated with the value of the standardized RG data. In the range of the value of the standardized RG data of 0.95 to 1.00, the value of the standardized RG data is associated with red.

In block S15, based on the table, a color corresponding to a value of the standardized RG data of the target pixel obtained in block S14 (standardization) is determined as a displaying color of the target pixel selected in block S12 (selection of target pixel) on the color map image.

<S16 in FIG. 2 (Judgment on Completion of Execution for All Pixels)>

In block S16, it is judged whether the blocks S12 to S15 have been processed for all the pixels of the current frame.

When an unprocessed pixel for the blocks S12 to S15 remains (S16: NO), the special image generation process in FIG. 2 returns to block S12 (selection of target pixel) to execute blocks S12 to S15.

<S17 in FIG. 2 (Calculation of Inflammation Evaluation Value Concerning Strength of Inflammation)>

Block S17 is executed when it is judged that the blocks S12 to S15 have been processed for all the pixels of the current frame (S16: YES). In block S17, an average value obtained by averaging the standardized RG data of the all the pixels of the current frame is calculated as an inflammation evaluation value, and display data of the calculated inflammation evaluation value is generated. It is noted that the process of calculating the inflammation evaluation value as the predetermined evaluation value regarding the color image executed in S17 is executed by the evaluation value calculator.

<S18 in FIG. 2 (Overlay Process)>

In block S18, using, as coefficients, an overlaying ratio between a normal image based on the image data input from the front stage signal processing circuit 220 (i.e., the image data having three color components of R, G and B) and the color map image based on the image data assigned the displaying colors in block S15 (determination of displaying color on color map image), the normal image data and the image data of the color map image are added together. In this case, a user is allowed to set or alter the coefficient through a user operation. In order to thickly display the normal image, a coefficient for the normal image data is set to be large. In order to thickly display the color map image, a coefficient for the color map is set to be large.

<S19 in FIG. 2 (Termination Judgment)>

In block S19, it is judged whether the operation mode of the electronic endoscope system 1 has been switched to a mode different from the special mode. When it is judged that the operation mode has not been switched to a mode different from the special mode (S19: NO), the special image generation process in FIG. 2 returns to block S11 (input of image data of current frame). When it is judged that the operation mode has been switched to a mode different from the special mode (S19: YES), the special image generation process in FIG. 2 terminates.

<Screen Display Example>

The rear stage signal processing circuit 240 generates an overlaid image of the normal image and the color map image based on the pixel data subjected to the adding process in block S18 (Overlay Process), and executes a masking process in which a peripheral area (a periphery of an image displaying area) of the displayed image is masked. Further, the rear stage signal processing circuit 240 generates the screen data for monitor representation in which the evaluation value of inflammation is overlaid on a masking area generated by the masking process. The rear stage signal processing circuit 240 converts the generated screen data for monitor representation into a predetermined video format signal, and transmits the converted signal to the monitor 300. It is noted that the image display for displaying the image in which the pixels of the inflammation portion and the pixels of the normal portion can be indicated by different colors so as to be distinguished from each other is, for example, the monitor 300.

Figure 5:
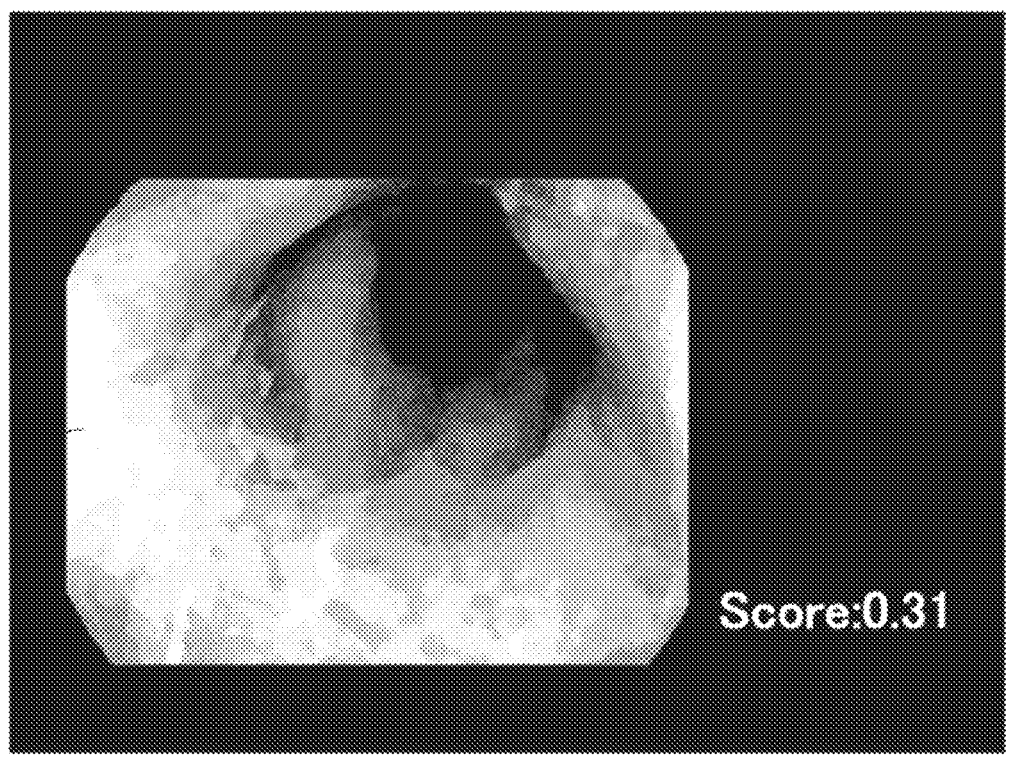
FIG. 5 illustrates an example of display screen displayed on a monitor in a special mode according to the embodiment of the disclosure.

FIG. 5 illustrates an example of onscreen representation in the special mode. As shown in FIG. 5, on the display screen of the monitor 300, the captured image (an overlaid mage in which the normal image and the color map image are overlaid) in the body cavity is displayed in a central portion and the peripheral portion of the image displaying area is masked. Further, in the masked area, the evaluation value (a score) of inflammation is displayed.

As described above, according to the embodiment, the evaluation value of inflammation (in this example, a value correlating to increase/decrease of hemoglobin color matter) can be obtained by executing a simple calculation without executing a non-linear calculation such as a tone enhancement process and a complicated color space conversion process. That is, hardware resources required for calculation of the evaluation value of inflammation can be reduced significantly. Furthermore, since the evaluation value of inflammation does not fluctuate depending on the capturing condition which would affect the brightness of the image, the operator is able to make an accurate and objective judgment.

More concretely, the endoscope system according to the embodiment brings following effects and/or solution of problems in the field of the present technique as described below. Firstly, the endoscope system according to the present embodiment serves as diagnosis support for early detection of inflammatory disease. Secondary, according to the configuration of the present embodiment, degree of inflammation is displayed on a screen, or an image of an area where inflammation occurs is highlighted so that an operator can discover mild inflammation which is hardily recognized visually. In particular, since the mild inflammation is difficult to be discriminated from a normal area, the effects brought by the configuration of the present embodiment regarding the evaluation of the mild inflammation is significant. Thirdly, according to the configuration of the present embodiment, it becomes possible to supply an objective evaluation value to a doctor as evaluation of the degree of the inflammation, differences of diagnosis among a plurality of doctors can be reduced. In particular, it is highly advantageous that the objective evaluation value, according to the configuration of the present embodiment, can be supplied to an inexperienced doctor. Fourthly, according to the configuration of the present embodiment, since an inflammation area can be displayed as an image in real time since load to image processing is reduced, diagnosis accuracy can be improved. Fifthly, according to the configuration of the present embodiment, since the load to the calculation of the evaluation value is lightened in comparison with the background technique mentioned above, a color map image (i.e., an image indicating the degree of inflammation) and a normal image can be displayed side by side, or in a synthesized manner without delay. As a result, it becomes possible to display the color map image without extending a diagnosis time period, and further, it becomes possible to avoid increase of burden to a patient.

The target areas of an observation according to the present embodiment includes, for example, respiratory organs, digestive organs and the like. The respiratory organs include, for example, lungs, ears, a nose and a throat. The digestive organs include, for example, a large bowel, a small bowel, a duodenum, and an uterus. It appears that the endoscope system according to the present embodiment has a significant effect when an observation target is the large bowel. It is so because of, concretely, the following reason. Firstly, regarding the large bowel, there are disease which can be evaluated based on the inflammation, and the advantage of discovering the inflammation area is larger in comparison of the other organs. Particularly, the inflammation evaluation value according to the present embodiment is effective as an index of inflammatory bowel disease (IBD) which is represented by the ulcerative colitis. Since no treatment method has been established for the ulcerative colitis, it is highly effective to discover the same and suppress advancing of the disease with use of the endoscope according to the configuration of the present embodiment. Since the large bowel is an organ which is relatively narrow and long organ in comparison with a stomach, an obtained image thereof has a depth, and the deeper a portion of the image is, the darker the image is. According to the present embodiment, it is possible to suppress variation of the evaluation value due to variation of the brightness in the image, a significant effect can be achieved by the present embodiment if the endoscope system according to the present embodiment is applied to observation of the large bowel. Thus, an aspect of the disclosure is that the endoscope system according to the present embodiment is of the respiratory organ or the digestive organ, and may be the large bowel.

It is generally difficult to diagnose a mild inflammation. However, according to the configuration of the present embodiment, for example, by displaying a result of evaluation of the degree of the inflammation, it becomes possible avoid a case where a doctor overlooks the mild inflammation. In particular, concerning the mild inflammation, a fact that decision criteria thereof is not clear is a definite factor to increase individual differences of diagnoses among doctors. Regarding this point, according to the configuration of the present embodiment, an objective evaluation value can be supplied to the doctors, variations of diagnosis among doctors can be reduced.

The above-described configuration of the present embodiment can be applied to calculation of evaluation values of not only the degree of inflammation, but various lesions associated with color change such as cancers and polyps, and advantageous effects as those described above can be brought. That is, the evaluation values according to the present embodiment are evaluation values of the lesions associated with the color change, and include the evaluation value of at least one of the cancers and the polyps.

The foregoing is the explanation about the embodiment of the disclosure. The disclosure is not limited to the above described embodiment, but can be varied in various ways within the scope of the disclosure. For example, the disclosure includes a combination of embodiments explicitly described in this specification and embodiments easily realized from the above described embodiment.

In the above described embodiment, the evaluation value of inflammation is calculated using an R component and a G component contained in each pixel; however, in another embodiment the evaluation value of inflammation may be calculated using an R component and a B component in each pixel in place of the R component and the G component.

In the above-described embodiment, the evaluation values of the inflammation and the like are calculated using the R, G and B primary color components. However, a configuration of calculating the evaluation values according to the present disclosure need not be limited to usage of the R, G and B primary color components. Instead of using the R, G and B primary color components, C (cyan), M (magenta), Y (yellow) and G (green) complementary color components may be used, and the evaluation values of the inflammation and the like may be calculated according to the method similar to that employed in the above-described embodiment.

In the above-described embodiment, a light source device including the lamp power igniter 206, the lamp 208, the collecting lens 210, the diaphragm 212, the motor 214 and the like is provided to the processor integrally therewith. However, the light source device may be provided as a device separated from the processor.

As described in the above-mentioned embodiment, instead of the CCD image sensor, the CMOS image sensor may be used as the solid state image pickup device 108. The CMOS image sensor generally has a tendency that the image becomes entirely darker in comparison with the CCD image sensor. Therefore, the advantageous effect of suppressing variation of the evaluation value depending on the brightness of the image according to the configuration of the above-described embodiment is exhibited more significantly in a case where the CMOS image sensor is used as the solid state image pickup device.

In order to perform diagnosis accurately, one may obtain a high-resolution image. Therefore, in view of improving the diagnosis accuracy, the resolution of the image may be one million pixels or more, the resolution may be two million pixels or more, and the resolution might be eight million pixels or more. The higher the resolution of the image is, the heavier the processing load for executing the above-described evaluation calculation for all the pixels is. However, according to the configuration of the above-described embodiment, the processing load can be suppressed, and the advantageous effects according to the configuration of the present embodiment in processing the high-resolution image is exhibited significantly.

In the special image processing according to the above-described embodiment, all the pixels in the image are subject to the image processing. However, pixels of extremely high brightness and extremely low brightness may be excluded from those subject to the processing. Specifically, for example, by making the pixels having brightness determined to be within a predetermined reference brightness range be subject to the evaluation value calculation, it becomes possible to improve accuracy of the evaluation values.

As mentioned in the above-described embodiment, various types of light sources can be used as the light source employed in the endoscope system 1. On the other hand, there could be a case where the type of the light source is limited (e.g., the laser being excluded as the type of the light source) depending on a purpose of observation of the endoscope system 1.

Regarding the color components used for calculating the evaluation value, there could be a case where calculation of the evaluation value using the hue and saturation.

The invention claimed is:

1. An endoscope system, comprising:
an image obtaining device configured to obtain a color image of a body cavity illuminated by white light, the color image including at least three color components;
an allocator configured to allocate, to each of a plurality of pixels constituting the color image, based on color components of the pixel, a corresponding point in a plane that includes a first axis, a second axis, and a third axis;
a distance data calculator configured to calculate, for each of the plurality of pixels, distance data representing a distance between the third axis and the point corresponding to the pixel along a line that is perpendicular to the third axis; and
an evaluation value calculator configured to calculate an evaluation value for the color image based on the calculated distance data for each of the plurality of pixels,
wherein the first axis is an axis of a first component of the at least three color components, the second axis is an axis of a second component of the at least three color components that intersects with the first axis, and the third axis passes through the intersection of the first axis and the second axis and is nonparallel with each of the first axis and the second axis, and
wherein the third axis extends in a direction of maximum sensitivity to brightness of the color image in the plane, and an axis orthogonal to the third axis extends in a direction of minimum sensitivity to brightness of the color image in the plane, and
wherein, for each of the plurality of pixels, the distance data indicates a degree of inflammation.

2. The endoscope system according to claim 1,
wherein the at least three color components include an R component, a G component and a B component,
wherein the first axis is an axis of the R component and the second axis is an axis of one of the G component and the B component.

3. The endoscope system according to claim 1, wherein the third axis forms 45 degrees with respect to the first axis and forms 45 degrees with respect to the second axis in the plane.

4. The endoscope system according to claim 1, wherein the distance data calculator is configured to calculate the distance data by subtracting a value of the second axis from a value of the first axis.

5. The endoscope system according to claim 1, wherein the evaluation value calculator is configured to use predetermined reference distance data to standardize the distance data and to calculate the evaluation value for the color image based on the standardized distance data of each of the plurality of pixels.

6. The endoscope system according to claim 1,
wherein the evaluation value includes an inflammation evaluation value indicating a degree of inflammation.

7. The endoscope system according to claim 6,
further comprising an image displaying device configured to display an image in which pixels of a normal portion and pixels of an inflammation portion are indicated in different colors so as to be distinguished from each other.

8. An evaluation value calculation device, comprising:
an allocator configured to allocate, to each of a plurality of pixels constituting a color image including at least three color components, based on color components of the pixel, a corresponding point in a plane that includes a first axis, a second axis, and a third axis;
a distance data calculator configured to calculate, for each of the plurality of pixels, distance data representing a distance between the third axis and the point corresponding to the pixel along a line that is perpendicular to the third axis; and
an evaluation value calculator configured to calculate an evaluation value for the color image based on the calculated distance data for each of the plurality of pixels,
wherein the first axis is an axis of a first component of the at least three color components, the second axis is an axis of a second component of the at least three color components that intersects with the first axis, and the third axis passes through the intersection of the first axis and the second axis and is nonparallel with each of the first axis and the second axis, and
wherein the third axis extends in a direction of maximum sensitivity to brightness of the color image in the plane, and an axis orthogonal to the third axis extends in a direction of minimum sensitivity to brightness of the color image in the plane, and
wherein, for each of the plurality of pixels, the distance data indicates a degree of inflammation.

9. The evaluation value calculation device according to claim 8,
wherein the third axis forms 45 degrees with respect to the first axis and forms 45 degrees with respect to the second axis in the plane.

10. The evaluation value calculation device according to claim 8,
wherein the distance data calculator is configured to obtain the distance data by subtracting a value of the second axis from a value of the first axis for each of the plurality of pixels.

11. The evaluation value calculation device according to claim 8,
wherein the evaluation value calculator is configured to use predetermined reference distance data to standardize the distance data and to calculate the evaluation value for the color image based on the standardized distance data of each of the plurality of pixels.

12. An evaluation value calculation device, comprising:
an allocator configured to allocate, to each of a plurality of pixels constituting a color image having red, green, and blue components, based on red, green, and blue components of the pixel, a corresponding point in a plane that includes a first axis, a second axis, and a third axis;
a distance data calculator configured to calculate, for each of the plurality of pixels, distance data representing a distance between the third axis and the point corresponding to the pixel along a line that is perpendicular to the third axis; and an evaluation value calculator configured to calculate an evaluation value for the color image based on the calculated distance data for each of the plurality of pixels, wherein the first axis is an axis of the red component, the second axis is an axis of the green component or of the blue component and is perpendicular to the first axis, and the third axis passes through the intersection of the first axis and the second axis and is nonparallel with each of the first axis and the second axis, and wherein the third axis extends in a direction of maximum sensitivity to brightness of the color image in the plane, and an axis orthogonal to the third axis extends in a direction of minimum sensitivity to brightness of the color image in the plane, and wherein, for each of the plurality of pixels, the distance data indicates a degree of inflammation.

13. The evaluation value calculation device according to claim 12, wherein the third axis forms 45 degrees with respect to the first axis and forms 45 degrees with respect to the second axis in the plane.

14. The evaluation value calculation device according to claim 12, wherein the distance data calculator is configured to calculate the distance data, for each of the plurality of pixels, by subtracting a value of the green component from a value of the red component.

15. The evaluation value calculation device according to claim 12, wherein the distance data calculator is configured to calculate the distance data, for each of the plurality of pixels, by subtracting a value of the blue component from a value of the red component.

16. The evaluation value calculation device according to claim 12, wherein the evaluation value calculator is configured to use predetermined reference distance data to standardize the distance data and to calculate the evaluation value for the color image based on the standardized distance data of each of the plurality of pixels.

* * * * *

UNITED STATES PATENT AND TRADEMARK OFFICE
CERTIFICATE OF CORRECTION

Page 1 of 1

PATENT NO. : 10,702,127 B2
APPLICATION NO. : 15/553966
DATED : July 7, 2020
INVENTOR(S) : Takao Makino It is certified that error appears in the above-identified patent and that said Letters Patent is hereby corrected as shown below:

On the Title Page

On page 2 Item (56) References Cited, subsection U.S. Patent Documents:

Please replace "2003/0071895 A1 4/2003 Ayame et al." with --2003/0071895 A1 4/2003 Higuchi et al.--

Please replace "2013/0051642 A1 2/2013 Kono et al." with --2013/0051642 A1 2/2013 Kanda et al.--

Please replace "2014/0320620 A1 10/2014 Yoshino et al." with --2014/0320620 A1 10/2014 Ikemoto et al.--

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*